United States Patent
Secrest et al.

(10) Patent No.: US 8,057,484 B2
(45) Date of Patent: Nov. 15, 2011

(54) RETRIEVAL DEVICE

(75) Inventors: Dean J. Secrest, Concord, OH (US); Christopher J. Kaye, Concord, OH (US); K. Randall John, Chardon, OH (US)

(73) Assignee: U.S. Endoscopy Group, Inc., Mentor, OH (US)

( * ) Notice: Subject to any disclaimer, the term of this patent is extended or adjusted under 35 U.S.C. 154(b) by 1346 days.

(21) Appl. No.: 11/137,763

(22) Filed: May 25, 2005

(65) Prior Publication Data
US 2005/0267489 A1    Dec. 1, 2005

Related U.S. Application Data

(60) Provisional application No. 60/574,072, filed on May 25, 2004.

(51) Int. Cl.
*A61B 17/24* (2006.01)
(52) U.S. Cl. .................. 606/113; 606/114; 606/127
(58) Field of Classification Search .................. 606/113, 606/114, 127, 128, 200, 46–52
See application file for complete search history.

(56) References Cited

U.S. PATENT DOCUMENTS

| | | | |
|---|---|---|---|
| 460,940 A | 10/1891 | Baugh | |
| 2,197,921 A | 4/1940 | Brown | |
| 2,626,447 A | 1/1953 | Hunt | |
| 5,098,441 A | 3/1992 | Wechler | |
| 5,147,371 A | 9/1992 | Washington et al. | |
| 5,354,303 A * | 10/1994 | Spaeth et al. | 606/128 |
| 5,449,372 A * | 9/1995 | Schmaltz et al. | 606/198 |
| 5,480,404 A | 1/1996 | Kammerer et al. | |
| 5,496,330 A | 3/1996 | Bates et al. | |
| 5,573,509 A * | 11/1996 | Thornton | 604/102.02 |
| 5,643,283 A * | 7/1997 | Younker | 606/17 |
| 5,759,187 A | 6/1998 | Nakao et al. | |

(Continued)

FOREIGN PATENT DOCUMENTS
DE    19938902    4/2000
(Continued)

OTHER PUBLICATIONS

International Search Report and Written Opinion of co-pending PCT International Patent Application No. PCT/US05/18497 mailed May 8, 2008.

(Continued)

*Primary Examiner* — Tuan Nguyen
(74) *Attorney, Agent, or Firm* — Calfee, Halter & Griswold LLP

(57) ABSTRACT

An endoscopic surgical device for retrieving objects, such as for example, severed human tissue, foreign objects or impacted food bolus, from within a subject is disclosed. The device includes a body and handle movable relative to the body, a tubular member fixed to the body, a link having a first end fixed to the handle and a second end remote from the body, and a net including a loop and a net element. The loop is expandable and collapsible by action of the handle relative to the body. The loop retains an expanded configuration when deployed to allow for the capture certain objects that were otherwise difficult to capture because of positioning, location, or object characteristics. The loop may be constructed of flat wire and form a polygon shape when deployed. Structure at the distal end of the loop may propel and retain the loop into an open position when in use in narrow organs such as the esophagus.

13 Claims, 3 Drawing Sheets

U.S. PATENT DOCUMENTS

| | | | |
|---|---|---|---|
| 5,782,840 A * | 7/1998 | Nakao | 606/114 |
| 5,906,621 A | 5/1999 | Secrest et al. | |
| 6,093,195 A | 7/2000 | Ouchi | |
| 6,235,026 B1 | 5/2001 | Smith | |
| 6,407,333 B1 | 6/2002 | Schroen | |
| 6,500,182 B2 | 12/2002 | Foster | |
| 6,527,781 B2 * | 3/2003 | Bates et al. | 606/127 |
| 6,814,739 B2 | 11/2004 | Secrest et al. | |
| 2003/0004538 A1 * | 1/2003 | Secrest et al. | 606/200 |
| 2005/0267489 A1 * | 12/2005 | Secrest et al. | 606/113 |

FOREIGN PATENT DOCUMENTS

| | | |
|---|---|---|
| EP | 0446020 A1 | 11/1991 |
| JP | 200352707 | 2/2003 |
| WO | 03105674 | 12/2003 |

OTHER PUBLICATIONS

Office Action from U.S. Appl. No. 10/965,542, mailed Jun. 25, 2008.
Office Action from U.S. Appl. No. 10/965,542, mailed Feb. 4, 2009.
Advanced Line Retrieval Devices Brochure, issued by US Endoscopy, 760204 Rev. A, date unknown.
Supplementary European Search Report from Application No. EP02 72 9222, mailed Aug. 20, 2009.

* cited by examiner

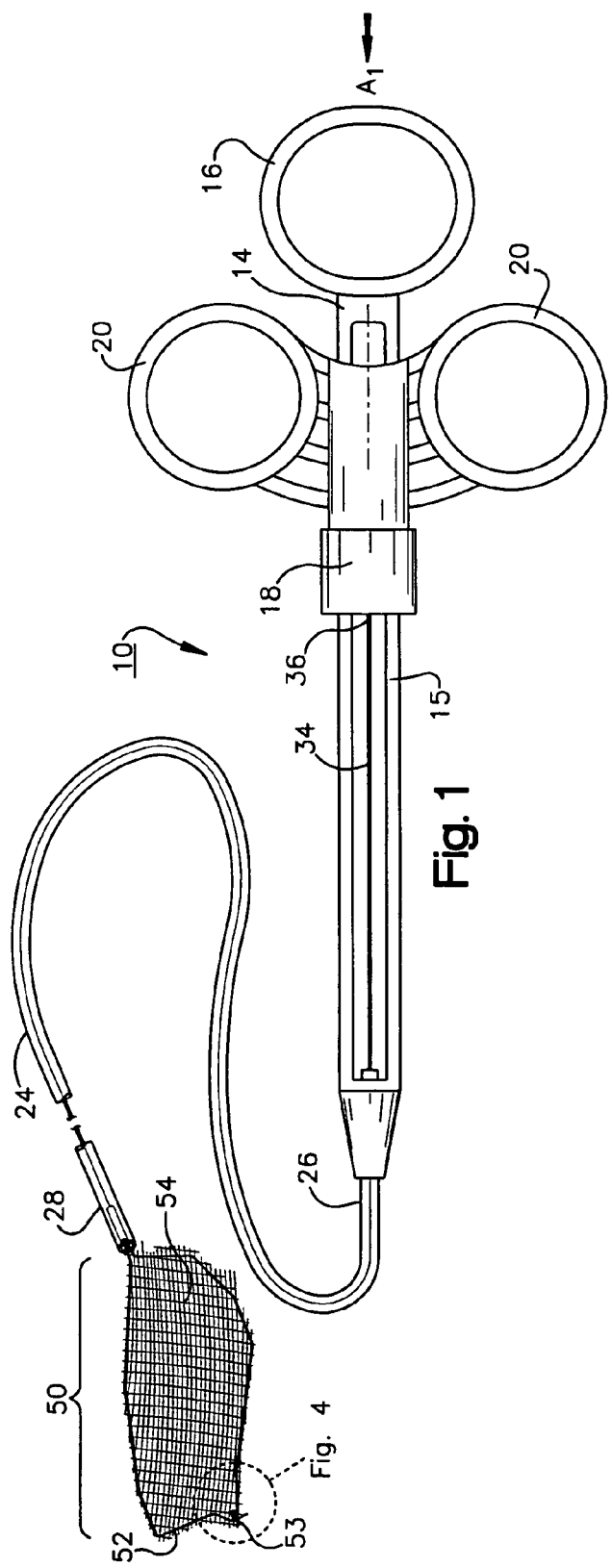
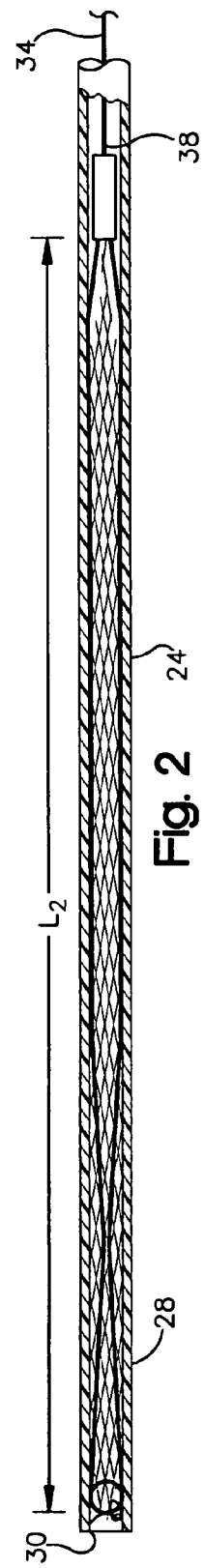
Fig. 1
Fig. 2

RETRIEVAL DEVICE

CROSS-REFERENCE TO RELATED APPLICATIONS

This non-provisional application claims the benefit of U.S. Provisional Patent Application No. 60/574,072, entitled "Retrieval Device," filed May 25, 2004, which is hereby incorporated in its entirety.

FIELD OF THE INVENTION

The present invention relates to a retrieval device and more particularly to a endoscopic retrieval device for retrieving objects from within a human subject.

BACKGROUND OF THE INVENTION

Endoscopic retrieval or removal devices are known in the art and are conventionally used to recover objects from inside a human subject. Such objects may include severed human tissue, foreign objects, or food bolus. Some typical devices include forceps or clasps to grab objects. Certain devices of this type are not well-suited for retrieving rounded or blunt foreign objects such as coins, marbles and batteries because they are difficult to hold secure. Further, if a foreign object is dropped near the trachea during the removal process the results can be catastrophic for the patient.

Devices using netting have been developed to capture rounded or blunt objects. U.S. Pat. No. 6,814,739 to Secrest et al., which is incorporated herein by reference in its entirety, discloses a device for retrieving an object from within a subject. In the use of devices having netting, and it is believed in the use of other devices, physicians have experienced difficulty in recovering certain objects, such as for example, impacted food bolus from the esophagus. A bolus is a mass of masticated or chewed food. In some cases, the bolus becomes impacted in the esophagus due to disease states, and other disorders and consequently, does not pass into the stomach. An object of this type may be more difficult to position over or be more heavier than the human tissue or foreign object for which these type of devices were designed. This problem is especially apparent when working in relatively tight places within the body. As a result, netting support collapses and does not retain its shape in a deployed position when holding the captured object.

To solve these and other problems, the present invention uses a flat wire to make the loop that supports the retrieval net. The flat wire provides a wider net capacity to entrap the bolus and is firmer, more rigid and less likely to collapse. As such, the loop maintains its shape in use, particularly when used in narrow lumens like the esophagus. The flat wire can be formed into a polygon shape, is more likely to be resistant to collapse and can include distal tip structure designed to further resist collapse and promote expansion.

SUMMARY OF THE INVENTION

In an illustrated embodiment of the invention, a device for retrieving objects, such as for example, impacted food bolus, foreign objects, and severed human tissue, is disclosed. The device is for use within an instrument channel of an endoscope during endoscopic medical procedures.

The device includes a body, a handle fixed to and movable relative to the body, an elongated tube fixed to the body, a link extending substantially through the tube and having a first end fixed to the handle and a second end remote from the body, and a net including a loop and a net element. The loop is expandable and collapsible by action of the handle relative to the body.

The loop retains an expanded configuration when deployed, allowing for relatively heavy objects to be disposed within the net element. The loop may be constructed from, for example, a stainless steel flat wire or other suitable material having a tensile strength greater than 300,000 psi.

The present invention is an improvement over prior art designs because the loop supporting the net is less likely to collapse under the weight of an object such as an impacted food bolus. Moreover, the wire opens wider than prior art designs when used in narrow lumens like the esophagus. The device allows for the capture of relatively heavy objects and reduces the risk associated with the procedure. Once an object is secured within the net element, the wire loop advantageously resists collapse.

Further features and advantages of the invention will become apparent from the following detailed description made with reference to the accompanying drawings.

The Detailed Description of the Invention merely describes preferred embodiments of the invention and is not intended to limit the scope of the claims in any way. Indeed, the invention as described by the claims is broader than and unlimited by the preferred embodiments, and the terms in the claims have their full ordinary meaning.

BRIEF DESCRIPTION OF THE DRAWINGS

FIG. 1 is a perspective view of a retrieval device constructed in accordance with an embodiment of the present invention;

FIG. 2 is a cross-sectional fragmentary view of the distal portion of the device illustrated in FIG. 1, showing a net in a stored position within a tube;

DESCRIPTION OF THE INVENTION

Figure 3:
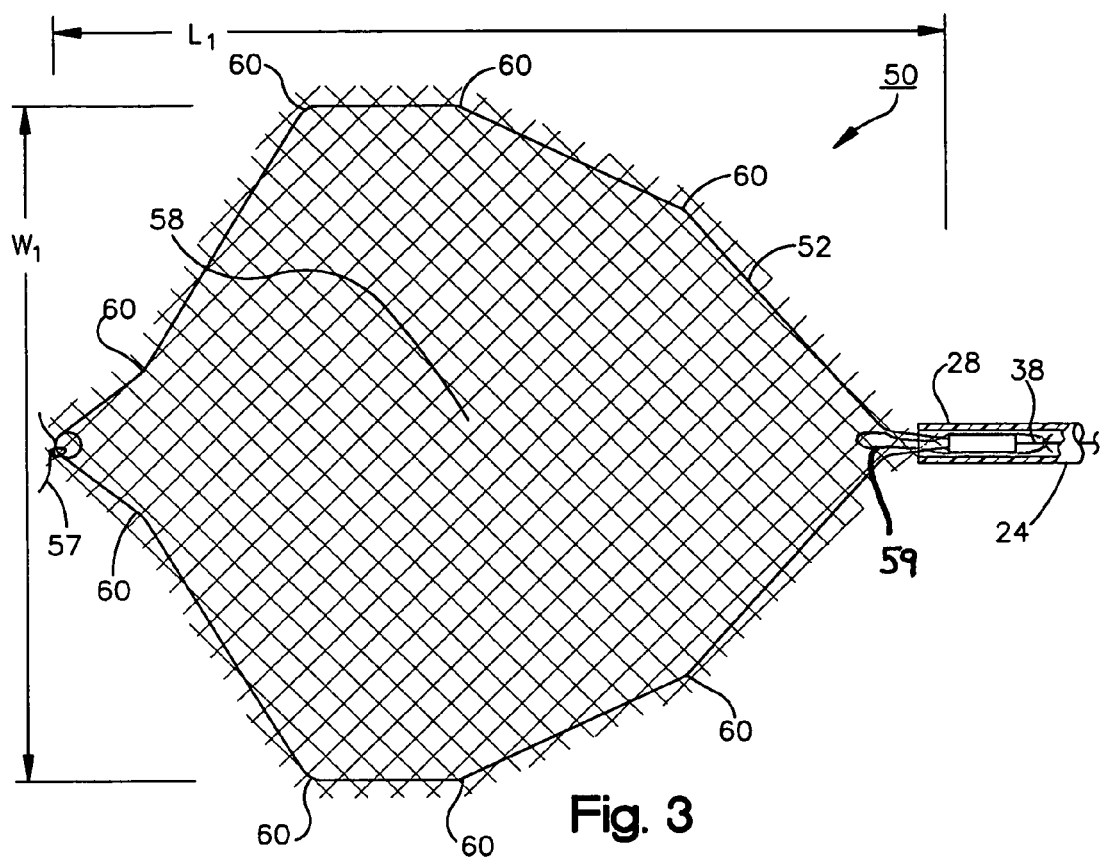
FIG. 3 is an alternative view of the portion illustrated in FIG. 2, showing the net in a deployed position outside of the tube.

A device for retrieving an object from within a human subject is disclosed. The device is designed for use within an endoscope and may be used for retrieving relatively heavy objects within relatively tight lumens, such as for example, impacted food bolus from the esophagus. In discussing the device, the terms distal and proximal are used with respect to the operator's hand. In other words, when the device is used within the auxiliary channel of an endoscope or similar device, the proximal and distal orientation are relative to the surgeon or operator of the device.

Referring now to the drawings, FIG. 1 is a perspective view of a retrieval device 10 constructed in accordance with an embodiment of the present invention. The device includes a support base or elongated body 14. The body includes a ring 16 at a proximal end. The device 10 also includes a handle 18 having two rings 20. The handle 18 is mounted over an interior section 15 of the body 14 and is movable relative to the body in the direction $A_1$ as illustrated. For example, an operator may place a finger in each of the rings 20 and thumb of the same hand in the body ring 16. By moving one's fingers in the direction $A_1$, an operator can move the handle 18 relative to the body 14. In contrast, the handle can be slid a direction opposite $A_1$ by pulling one's finger's towards one's thumb.

The device includes an elongated inducer member or tubular member 24 having a first end 26 fixed to the body 14 and a second end 28. The tubular member 24 and the body are a fixed support assembly for the moving parts of the device. The tubular member 24 may be any suitable small diameter tube formed of a non-reactive low-friction plastic material, such as for example, polytetrafluouroethylene. The tubular member 24 defines a passage with an opening 30 at the tubular member second end 28, as best seen in FIG. 2 which shows cross-sectional view of a distal portion of the device 10.

A motion transmitting link 34 is connected to the handle 18. The link 34 has a first end 36 fixed to the handle 18 and a second end 38 remote from the body 14. As shown in the drawings, the link extends substantially through the tubular member 24 passage. The link may be constructed of any suitable rigid material.

Still referring to FIG. 1, the device also includes a net 50. The net is used by the operator to capture and retrieve objects from within a human subject. The net 50 includes a loop 52 and a net element 54 secured to the loop 52. The loop may be inserted through a mouth section of the net or otherwise connected in any conventional manner known in the art. As shown in several Figures, a net tether 57 at the distal end of the net anchors the net element 54 to the loop 52 at a distal end 53 of the loop.

As discussed, the net is designed for movement between two positions. FIGS. 1 and 2 shows the net 50 in these two possible positions. FIG. 1 shows the net 50 in a deployed position. In this position, the net has a length $L_1$ and a width $W_1$. The ratio of $L_1$ and a width $W_1$ is less than prior art designs, meaning the device has increased width capacity. FIG. 2 is a cross-sectional view of a distal portion of the device 10, showing the net in a stored position within the tube 24. In this position, the net has a length $L_2$ which is considerably longer than $L_1$. As shown in FIG. 2, the net 50 is disposed adjacent the link 34 second end 38 for deployment and retrieval through the tubular member passage opening 30. By movement of the handle 18 relative to the body 14, the net is movable between either the deployed or stored positions.

Figure 4:
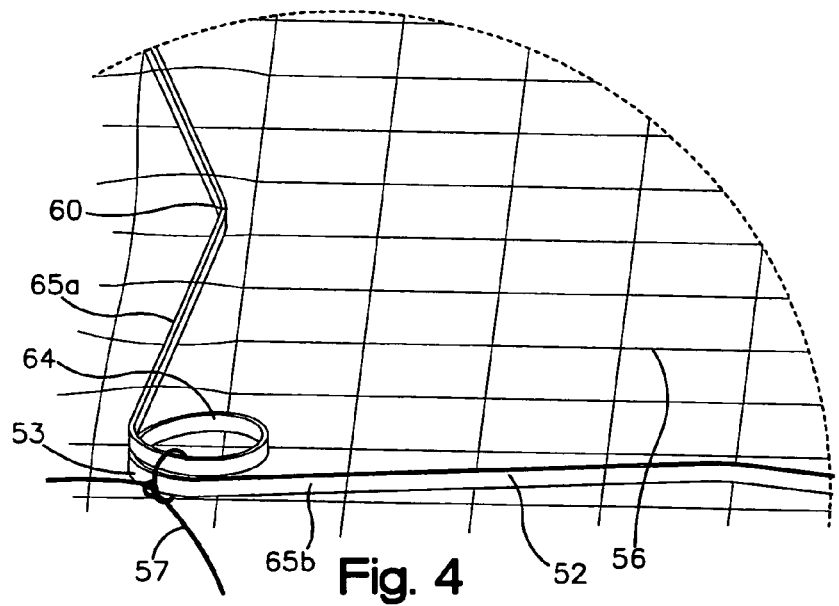
FIG. 4 is an exploded perspective view of the designated circular section of FIG. 1, showing detail of the net element and the distal end of the loop.
Figure 7:
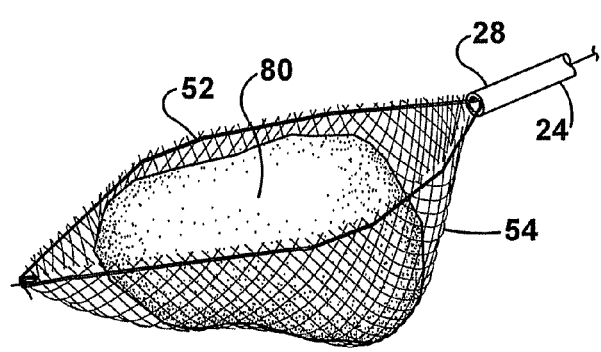
FIG. 7 is a perspective view of a distal portion of the device illustrated in FIG. 4, showing a food bolus captured within the net.

Referring now to FIG. 3, the net 50 is illustrated in a deployed position and fully expanded outside of the tube 24 second end 28. The net element 54 may be constructed of any suitable light weight material, such as for example, nylon mesh string 56, as best seen in FIG. 4. The net element 54 has a centrally located object receiving pouch section 58. To be discussed further in greater detail, captured objects rest within this section as shown in FIG. 7.

As discussed, the net 50 includes a loop 52. The loop 52 acts as a support for the net 50 when deployed. The loop 52 is resiliently movable between a collapsed position shown in FIG. 2 to an expanded position shown in FIG. 3 by operator action of the handle relative to the body. A distal end 53 includes structure to resist collapse during use.

Referring now to FIG. 4, an exploded perspective view of the designated circular section of FIG. 1 is shown. In the embodiment shown, the loop 52 is a flat wire constructed of a resilient material, such as for example, 304 stainless steel. The loop material may be constructed from a material having a tensile strength greater than 300,000 psi.

Referring again to FIG. 3, the loop 52 includes collapse-resistant bends 60, with the straight segments between the bends 60 forming a polygon shape. As apparent from FIG. 3, a maximum width $W_1$ of the loop 52 is defined by two opposing linear segments of the polygon. As shown, the two opposing linear segments are also parallel. In regard to these two linear segments, the distance along a longitudinal axis of the loop 52 from a distal most point of each linear segment to a distal most point of the loop is less than the distance from a proximal most point of each linear segment to a proximal most point of the loop. In other words, FIG. 3 illustrates a majority of each of the two opposing linear segments disposed closer to the distal end of the loop 52 as compared to the proximal end of the loop 52. This positioning is apparent from their relative placement along the length $L_1$ of the loop 52.

Other features of the invention are apparent from FIG. 3. As previously stated, the polygon shape of the support loop defines a pair of lengthwise extending parallel linear wire segments that define a maximum width $W_1$ of the support loop 52. Additional linear wire segments which extend distally from an end of each of the parallel wire segments taper distally to connect with the spiral wire structure. Additional linear wire segments which extend proximally from an end of each of the parallel wire segments taper proximally to connect within the introducer passage opening.

The loop 52 is illustrated having a first and a second support loop portion in FIG. 3. The first support loop portion is "V" shaped and flares outwardly in a distal direction from the elongated hollow tube 24, with a pair of lengthwise parallel wire segments at a widest portion $W_1$ of the "V" shape. The second support loop portion is "V" shaped and flares outwardly in a proximal direction from the spiral spring 64 to connect with a distal end of each parallel wire segment of the lengthwise parallel wire segments. The collapse resistant bends 60 and the linear wire segments located between the spiral spring and each of the parallel wire segments are oriented to "V" inward, as seen in FIG. 4, into the net. Also, the second support loop portion is shorter along a net length $L_1$ than the first support loop portion.

The illustrated device in FIGS. 2 and 3 includes several features that promote expansion and prohibit collapse when an object is held within the net element or the device is used in a relatively tight lumen. The loop 52 includes several collapse-resistant bends 60. The location of the bends 60 act as memory points and are retained by the loop through multiple deployments. These bends are constructed such that the loop forms a polygon shape when deployed. As shown, the loop 52 forms a general hexagon shape. It is believed that the polygon shape is more resilient and less likely to collapse when an object is held within the net or when retrieving an object within a narrow lumen. It should be understood by those with ordinary skill in the art that the polygon shape shown in FIG. 3 is for exemplary purposes only, and other polygon shapes can be used in the practice of the present invention.

As best shown in FIG. 4, the loop 52 further includes a 360 degree curved portion 64 disposed at a distal end 53 of the loop. It is believed that this curved portion 64 acts as a spring tip to further prohibits collapse when an object is held within the net. It is also believed that this spring tip 64 acts to promotes polygon segments 65a, 65b to remain apart during deployment. This feature is beneficial in tight lumens, such as for example, the esophagus.

Figure 5:
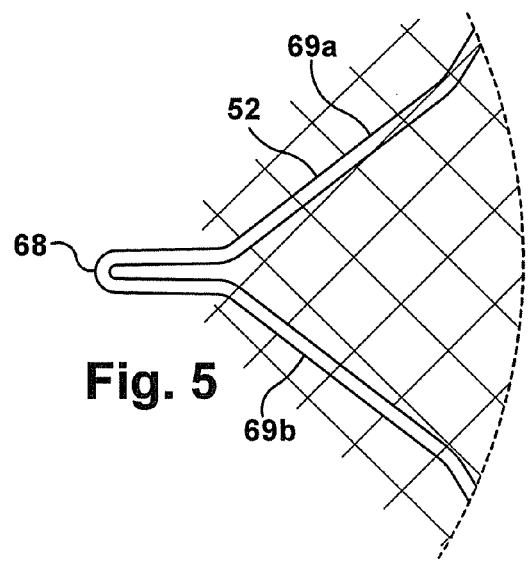
FIG. 5 is a exploded fragmentary top view of the net of a retrieval device, showing an alternative structure of the distal end of the loop.

Several other embodiments include alternative shapes and structures of the distal end of the loop. FIG. 5 shows the distal end of the support wire in an alternative shape. The loop 52 is bent to form a protruding tip 68. It is believed that this shape promotes polygon segments 69a, 69b to remain apart during deployment and use.

Figure 6:
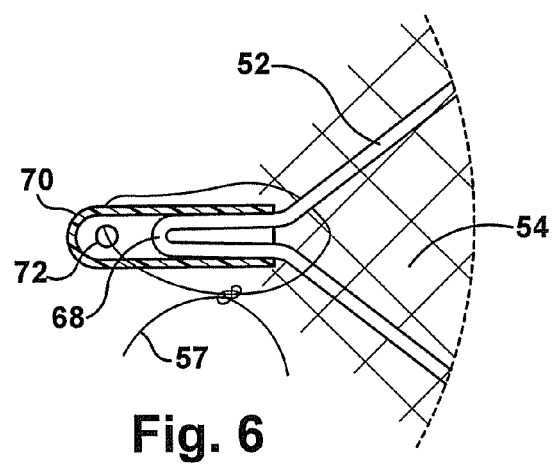
FIG. 6 is a exploded fragmentary top view of the net of a retrieval device, showing yet another alternative structure of the distal end of the loop.

Referring to FIG. 6, an exploded fragmentary view of other alternative structure of the distal end 53 of the loop 52 is shown. As in the embodiment shown in FIG. 5, the distal end of the loop 52 is bent into a protruding tip 68. Over the spring tip 68, a tip cap member 70 is press fit or connected by another suitable technique. The tip 70 may be constructed of plastic or any other suitable material. The tip 70 includes an aperture 72 therethrough as a distal end. As shown, the net anchor 57 is placed through the aperture and tied off to secure the net element 54 to the loop 52. A corresponding anchor 59 can be used to tie off the net element 54 to the link 34 on the proximal side of the wire loop connector.

In an exemplary operation of the device, the patient is intubated with an endoscope. The device 10 is inserted through an auxiliary channel of the endoscope, either before or after intubation. The device is inserted with the net 50 in a stored position as shown in FIG. 2. The surgeon utilizing the optical features of the endoscope will identify the object for removal. After identification, the surgeon with manipulate the handle 18 with respect to the base 14 to deploy the net 50 into the position shown in FIG. 1.

The surgeon will manipulate the object into the receiving pouch 58 by one of a variety of techniques, including the use of additional endoscopic tools. The surgeon may manipulate the snare over the top of the object and enclose the net, or manipulate the snare under the object and enclose the net. Further, the surgeon may use the net as a scoop, relying on the increased lateral stability of the device over prior art designs. Once the object is within the pouch, the surgeon may manipulate the handle with respect to the body to slightly close the net around the object. FIG. 7 is a perspective view of a distal portion of the device illustrated in FIG. 4, showing a food bolus captured within the net. In this position, the loop retains an expanded configuration with an object 80 retained within the pouch section 58. The endoscope now may be removed from the patient with risk of loss of the food bolus greatly reduced as compared to prior art devices.

While several embodiments of the invention has been illustrated and described in considerable detail, the present invention is not to be considered limited to the precise construction disclosed. Various adaptations, modifications and uses of the invention may occur to those skilled in the arts to which the invention relates. It is the intention to cover all such adaptations, modifications and uses falling within the scope or spirit of the claims filed herewith.

What is claimed is:

1. A device for use within an instrument channel of an endoscope for retrieving objects from within a human body, the device comprising:
   a. a body;
   b. a handle mounted to and movable relative to said body;
   c. a tubular member having a first end fixed to said body and a second end, the tubular member defining a passage and opening at said second end;
   d. a link having a first end fixed to said handle and a second end remote from said body, said link extending substantially through said tubular member passage; and
   e. a net comprising a loop and a net element secured to said loop and having an object receiving pouch section, said net disposed adjacent said link second end for deployment and retrieval through said tubular passage opening;
   f. said loop being expandable to a polygon shape formed by a plurality of linear segments separated by collapse-resistant bends and said loop being collapsible by action of said handle relative to said body, wherein said loop comprises a piece of wire having a single spiral wire structure located at a distal end of said loop;
   g. wherein said loop has a maximum width defined by two opposing linear segments of the polygon shape, wherein a distance along a longitudinal axis of the loop from a distal most point of each linear segment to a distal most point of the loop is less than the distance from a proximal most point of each linear segment to a proximal most point of the loop.

2. The device of claim 1 wherein said loop is constructed from a flat wire.

3. The device of claim 1 wherein said loop is constructed from a flat wire comprising at least one collapse-resistant bend.

4. The device of claim 1 wherein net is anchored to said single spiral wire structure.

5. The device of claim 1 wherein said net comprises a plastic tip disposed at said distal end of said loop and having an aperture therethrough, wherein a net anchor is routed through said aperture to secure said net element to said plastic tip.

6. The device of claim 1 wherein said loop retains an expanded configuration when an object retained within said pouch section.

7. An endoscopic device for retrieving an object from within a patient's body, the device comprising:
   a. a support unit comprising:
      i. a body; and
      ii. an elongated introducer member having a first end section proximal and fixed with respect to said body and a second end section remote from the body, the introducer member defining a passage and opening at said second end section; and
   b. a tissue retrieving net system comprising:
      i. a net comprising a resilient wire support loop and a net element having a mouth section slidably disposed on the support loop and a tissue receiving pouch section, said net disposed adjacent said introducer member second end for deployment and retrieval through said introducer passage opening;
      ii. a net deployment and retrieval assembly extending substantially through said introducer passage and connected to the net, said assembly comprising a motion transmitting link extending in said introducer passage to said support loop; and
      iii. a net actuator unit comprising a handle fixed with respect to said motion transmitting link and movable relative to said body so that shifting said handle relative to said body shifts said net into and out of said introducer passage opening;
   c. said introducer member passage having an internal diameter substantially smaller than the width of said support loop when said support loop is deployed, said introducer member engaging said support loop at said opening and resiliently collapsing and elongating said support loop as said net is retrieved and moves into said introducer member passage, said support loop resiliently returning to an uncollapsed configuration as it is deployed;
   d. said net system further comprising a net controller for assuring that said net mouth extends fully about said support loop when said support loop is deployed, said controller comprising a net tether anchored at a distal end of said loop;

e. wherein said support loop and net element is expandable to a polygon shape that is formed by a plurality of linear wire segments separated by collapse-resistant bends with a distal end of said support loop comprising a collapse-resistant spiral bend defining at least 360 degrees of a spiral wire structure;

f. further wherein said polygon shape of said support loop has a pair of lengthwise extending parallel linear wire segments that define a maximum width of said support loop, wherein said linear wire segments extending distally from an end of each of said parallel wire segments taper distally to connect with said spiral wire structure to define a first slope, and said linear wire segments extending proximally from an end of each of said parallel wire segments taper proximally to connect within said introducer passage opening, to define a second slope, wherein said first slope is steeper than said second slope.

8. The device of claim 7 wherein said loop is constructed from a flat wire.

9. The device of claim 7 wherein said net is anchored to said collapse-resistant spiral bend.

10. The device of claim 7 wherein said net comprises a tip member disposed at said distal end of said loop and having an aperture therethrough, wherein a net anchor is routed through said aperture to secure said net element to said tip member.

11. The device of claim 7 wherein said loop retains an expanded configuration when an object is disposed within said pouch section.

12. An endoscopic device for retrieving objects from within a human body, the device comprising:
   a. a support assembly comprising a base and an elongated hollow tube;
   b. a transmitting assembly comprising a handle movable relative to said base and a link having a first end fixed to said handle and a second end remote from said base, said link extending substantially through a length of said tube; and
   c. a net comprising a support loop defining a loop opening and a net element secured across said loop opening of said support loop, said loop being movable between an expanded position and a collapsed position by action of said handle relative to said base to move the net element from an open to a closed position;
   d. wherein said loop is polygon shaped in said expanded position and is formed by a plurality of linear segments separated by collapse-resistant bends to define a loop opening, and said loop comprises a torsion spring tip at a distal end thereof;
   e. further wherein said loop has a maximum width defined by two opposing linear segments of the polygon shape, wherein a majority of each linear segment is disposed closer to the distal most point of the loop than the proximal most point of the loop.

13. A device for use within an instrument channel of an endoscope for retrieving objects from within a human body, the device comprising:
   a. a body;
   b. a handle mounted to and movable relative to said body;
   c. a tubular member having a first end fixed to said body and a second end, the tubular member defining a passage and opening at said second end;
   d. a link having a first end fixed to said handle and a second end remote from said body, said link extending substantially through said tubular member passage; and
   e. a net comprising a loop and a net element secured to said loop and having an object receiving pouch section, said net disposed adjacent said link second end for deployment and retrieval through said tubular passage opening;
   f. said loop being expandable to a polygon shape formed by a plurality of linear segments separated by collapse-resistant bends and said loop being collapsible by action of said handle relative to said body, wherein said loop comprises a piece of wire having a single spiral wire structure located at a distal end of said loop;
   g. wherein said plurality of linear wire segments separated by collapse-resistant bends defines a support loop for said net element having:
      i) a first support loop portion that is "V" shaped and flares outwardly from said elongated hollow tube with a pair of lengthwise parallel wire segments at a widest portion of said "V"; and
      ii) a second support loop portion that is "V" shaped to flare outwardly from said spiral spring to connect with a distal end of each parallel wire segment of said lengthwise parallel wire segments;
      iii) wherein said collapse resistant bends and said linear wire segments located between said spiral spring and each of said parallel wire segments are oriented to "V" inward into said net and said second support loop portion is shorter along a net length than said first support loop portion.

* * * * *